US011029263B2

(12) United States Patent
Fung et al.

(10) Patent No.: US 11,029,263 B2
(45) Date of Patent: Jun. 8, 2021

(54) SYSTEMS AND METHODS FOR INSPECTION USING ELECTROMAGNETIC RADIATION

(71) Applicant: Integrated-X, Inc., San Diego, CA (US)

(72) Inventors: Henry Fung, San Diego, CA (US); Bruk Sahilu, San Diego, CA (US); Valentin Macavei, Signal Hill, CA (US); Huy Ly, Santee, CA (US)

(73) Assignee: Integrated-X, Inc., San Diego, CA (US)

( * ) Notice: Subject to any disclaimer, the term of this patent is extended or adjusted under 35 U.S.C. 154(b) by 995 days.

(21) Appl. No.: 15/373,252

(22) Filed: Dec. 8, 2016

(65) Prior Publication Data

US 2017/0168171 A1 Jun. 15, 2017

Related U.S. Application Data

(60) Provisional application No. 62/265,004, filed on Dec. 9, 2015.

(51) Int. Cl.
*G01N 23/044* (2018.01)
*G01T 1/29* (2006.01)
(Continued)

(52) U.S. Cl.
CPC ......... *G01N 23/044* (2018.02); *G01T 1/2921* (2013.01); *G01T 7/00* (2013.01);
(Continued)

(58) Field of Classification Search
CPC . G01T 7/00; G01T 1/2921; G01N 2033/0093; G01N 23/04; G01N 33/00;
(Continued)

(56) References Cited

U.S. PATENT DOCUMENTS 6,081,577 A * 6/2000 Webber ................ G01N 23/046 378/23
6,459,760 B1 * 10/2002 D'Ambrosio .......... G01N 23/04 378/43

(Continued)

FOREIGN PATENT DOCUMENTS

| | | | |
|---|---|---|---|
| WO | 2002057726 | A2 | 7/2002 |
| WO | 2004086210 | A1 | 10/2004 |
| WO | 2012004342 | A1 | 1/2012 |

OTHER PUBLICATIONS

International Search Report and Written Opinion for international patent application No. PCT/US2016/065659 from the Korean International Searching Authority dated Mar. 29, 2017.

*Primary Examiner* — Dani Fox
*Assistant Examiner* — Soorena Kefayati
(74) *Attorney, Agent, or Firm* — Procopio, Cory, Hargreaves & Savitch LLP

(57) ABSTRACT

This disclosure provides a system and method for inspecting a component. The device can have a detector positioning system coupled to a detector and operable to move the detector within five degrees of freedom. The device can have an emitter positioning system operably coupled to the emitter and operable to move the emitter in three dimensions. The device can move the detector to a reference point above the component, the reference point being separated by a radius (ρ) on the applicate axis from an inspection point on the component. The controller can also receive at least one input from a display, and command the detector to a detector position within a spherical dome centered on the reference point based on the at least one input.

21 Claims, 7 Drawing Sheets

100
134
(X,Y,ρ)
Z
132a
X
130
130
132b
B
Y
132c
A
131
136
138
139
α
ρ
133
110
102
114
112
116
124
β
122
104
(X,Y)
120
Emitter
Y
X

(51) Int. Cl.
*G01T 7/00* (2006.01)
*H04N 5/32* (2006.01)
*G01N 33/00* (2006.01)

(52) U.S. Cl.
CPC ............... *H04N 5/32* (2013.01); *G01N 33/00* (2013.01); *G01N 2033/0093* (2013.01)

(58) Field of Classification Search
CPC ...... G01N 23/044; H04N 5/32; G01R 31/311; G01R 31/31728
See application file for complete search history.

(56) References Cited

U.S. PATENT DOCUMENTS 6,977,985 B2 * 12/2005 Bohn ................... G01N 23/044 378/27
7,590,218 B2 * 9/2009 Scherch ............... A61N 5/1049 378/205
8,352,073 B2 * 1/2013 Berti ...................... G21K 1/065 700/248
9,055,886 B1 * 6/2015 Garretson ................ A61B 6/04
10,338,238 B2 * 7/2019 Kim ......................... A61B 6/44
2002/0191750 A1 * 12/2002 Wang ....................... A61B 6/06 378/152
2004/0234025 A1 * 11/2004 Schroeder ............. A61B 6/032 378/20
2005/0157841 A1 * 7/2005 Chopra ................ G01N 23/044 378/22
2006/0285641 A1 * 12/2006 Scherch ................ A61B 5/064 378/65
2007/0189450 A1 * 8/2007 Nakai .................. G01N 23/044 378/51
2007/0280414 A1 * 12/2007 Sasayama ............ G01N 23/223 378/45
2008/0232551 A1 * 9/2008 Peecock ............... G01N 23/207 378/195
2009/0216373 A1 * 8/2009 Berti ...................... B25J 9/1694 700/258
2009/0296886 A1 * 12/2009 Maltz ................... A61B 6/4458 378/65
2010/0142672 A1 * 6/2010 Crowley .............. G01N 23/044 378/24
2010/0172561 A1 * 7/2010 Ota ......................... H01L 22/00 382/131
2010/0329532 A1 * 12/2010 Masuda ................. A61B 6/466 382/132
2011/0222650 A1 * 9/2011 Muenker .............. G01N 23/046 378/20
2011/0243299 A1 * 10/2011 Sugita .................. G01N 23/046 378/19
2011/0255660 A1 * 10/2011 Masuda ................. G01N 23/04 378/22
2012/0201352 A1 * 8/2012 Dennerlein .......... A61B 6/4452 378/62
2013/0108017 A1 * 5/2013 Golubovic ............ G06T 7/0008 378/41
2014/0037057 A1 * 2/2014 Kim ....................... A61B 6/469 378/62
2014/0205058 A1 * 7/2014 Tagawa ................. G06T 11/005 378/11
2014/0334605 A1 * 11/2014 Ookawa ............... H05K 13/082 378/62
2015/0131778 A1 * 5/2015 Lowe ................... G01N 23/046 378/37
2015/0204801 A1 * 7/2015 Itou ...................... H05K 13/082 378/63
2015/0247946 A1 * 9/2015 Garretson ........... H01J 37/3045 378/87
2015/0369757 A1 * 12/2015 Golubovic ........... G01N 23/046 378/19
2016/0146968 A1 * 5/2016 Schuff .................... B65G 15/28 378/69
2016/0170075 A1 * 6/2016 Schafer .............. G01N 23/2209 378/9
2016/0247325 A1 * 8/2016 Yu .......................... A61B 6/037
2016/0363544 A1 * 12/2016 Tagawa ................ G01N 23/046
2017/0011973 A1 * 1/2017 Tingay ................... G01N 23/04
2017/0219499 A1 * 8/2017 Tanaka .................. G01N 23/04

* cited by examiner

SYSTEMS AND METHODS FOR INSPECTION USING ELECTROMAGNETIC RADIATION

CROSS REFERENCE TO RELATED APPLICATIONS

This application claims priority to U.S. Provisional Application 62/265,004, filed Dec. 9, 2015, entitled "Systems and Methods for X-Ray Inspection," the contents of which are hereby incorporated by reference in their entirety.

BACKGROUND

Technological Field

This disclosure relates to electromagnetic (EM) inspection systems and devices. More specifically, this disclosure relates to motion control systems and methods for electromagnetic inspection devices.

Related Art

Some electromagnetic (e.g., x-ray) inspection systems use can implement various control devices, such as joysticks and switches, for motion control. In some examples, these input devices or control devices can control the movement of an x-ray emitter. The control devices can also control the platform upon which the component being inspected is placed.

The system can provide visual feedback to the operator in the form of an x-ray image. Such an x-ray image can be displayed via a separate viewing application on a display coupled to the x-ray camera. The viewing application can have additional functionality, such as, for example, image processing tools, built into the system via various menus or options. Some systems have extensive numbers of such menus and options that can be selected by buttons or other interface features.

This type of interface can require an operator to control the movement of the x-ray emitter and/or inspected component in a physically different location than the viewing application and on a separate set of controls. This presents a contextual disconnect for the operator being separated from the control display. Furthermore, user interfaces for these viewing applications are often built without regard for human factors, and lack an intuitive user experience due to the sheer number of menus and buttons that will overwhelm an operator.

SUMMARY

In general, this disclosure describes systems and methods related to systems and methods for inspection using electromagnetic radiation. The systems, methods and devices of this disclosure each have several innovative aspects, no single one of which is solely responsible for the desirable attributes disclosed herein.

One aspect of the disclosure provides a x-ray inspection system. The x-ray inspection system can have an inspection platform for supporting a component to be inspected. The x-ray inspection system can have an x-ray emitter configured to generate an inspection beam and disposed on a first side of the inspection platform. The x-ray inspection system can have a detector configured to detect the inspection beam. The detector can be disposed on a second side of the inspection platform, opposite the first side of the inspection platform. The x-ray inspection system can have a detector positioning system coupled to the detector and operable to move the detector on an abscissa axis, an ordinate axis, and an applicate axis. The x-ray inspection system can have an emitter positioning system operably coupled to the emitter and operable to move the emitter in the abscissa axis and the ordinate axis and the applicate axis. The x-ray inspection system can have a controller coupled to the emitter positioning system and the detector positioning system. The controller can receive at least one input from an interface. The controller can command the detector positioning system to move the detector to a reference point aligned with the emitter, the reference point being separated by a radius (ρ) on the applicate axis from an inspection point on the component indicated by the at least one input. The controller can command the detector positioning system to move the detector to a detector position within a spherical dome centered on the reference point based on the at least one input Another aspect of the disclosure provides a method for X-ray inspection of a component. The method can include receiving first input at a touch screen display indicating an inspection point on the component. The method can include calculating, at a controller, a reference point aligned the inspection point, the reference point having a position at a radius (ρ) on an applicate axis away from the inspection point. The method can include moving the detector to the reference point, the detector being disposed on a first side of the component. The method can include moving an emitter on an abscissa axis and an ordinate axis based on the inspection point, the emitter being disposed on a second side of the component opposite the first side. The method can include receiving second input at the display indicating a skewed viewing angle of the inspection point. The method can include calculating, at the controller, a detector position based on the skewed viewing angle. The detector position can be located on a curved plane. The curved plane can be described by a spherical dome having the radius (ρ) from the inspection point and centered on the reference point. The method can include moving the detector to the detector position.

Another aspect of the disclosure provides a device for inspecting a component. The device can have an inspection platform operable to support the component. The device can have an emitter disposed on a first side of the inspection platform, the emitter configured to emit an inspection beam toward the component. The device can have a detector disposed on a second side of the inspection platform, opposite the first side. The detector can detect at least a portion of the inspection beam that penetrates the component. The device can have a detector positioning system operably coupled to the detector and operable to move the detector on an abscissa axis, an ordinate axis, and an applicate axis. The device can have an emitter positioning system operably coupled to the emitter and configured to move the emitter in the abscissa axis, the ordinate axis, and the applicate axis. The device can have a controller operably coupled to the emitter positioning system and the detector positioning system. The controller can receive a first input indicating an inspection point on the component. The controller can command, via the detector positioning system, the detector to a reference point aligned with the inspection point, the reference point being separated by a radius (ρ) on the applicate axis from the inspection point. The controller can move the emitter to a point on the abscissa axis and the ordinate axis based on the inspection point. The controller can receive a second input indicating a modified viewing angle of the inspection point. The controller can command, via the detector positioning system, the detector to a detector position within a spherical dome centered on the reference point. The spherical dome can be defined by an emitter beam width and the radius (ρ).

Other features and advantages of the present disclosure should be apparent from the following description which illustrates, by way of example, aspects of the disclosure.

BRIEF DESCRIPTION OF THE FIGURES

The details of embodiments of the present disclosure, both as to their structure and operation, may be gleaned in part by study of the accompanying drawings, in which like reference numerals refer to like parts, and in which.

DETAILED DESCRIPTION

The detailed description set forth below, in connection with the accompanying drawings, is intended as a description of various embodiments and is not intended to represent the only embodiments in which the disclosure may be practiced. The detailed description includes specific details for the purpose of providing a thorough understanding of the embodiments. In some instances, well-known structures and components are shown in simplified form for brevity of description.

Figure 1:
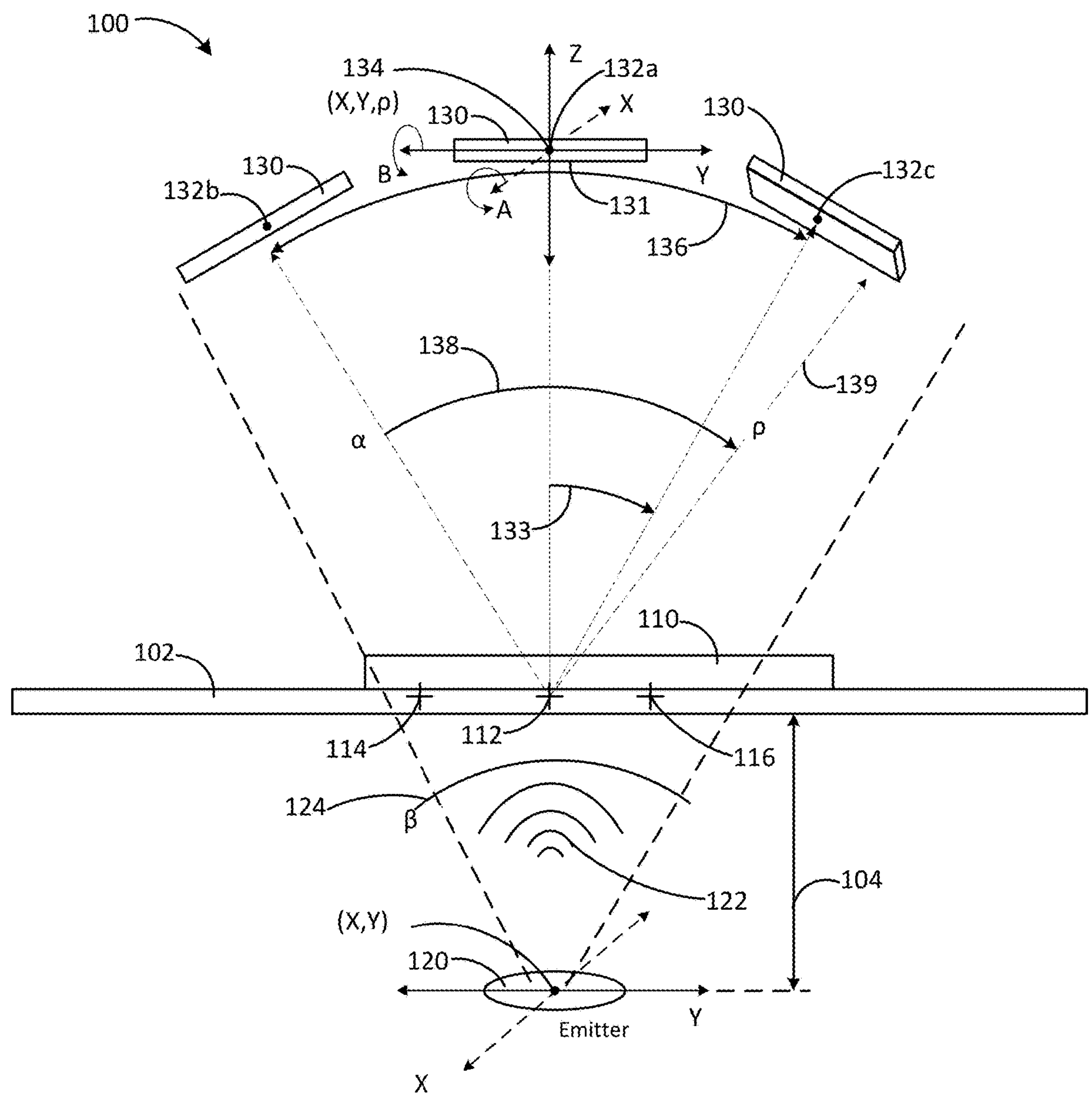
FIG. 1 is a graphical representation of a device for inspecting a component.

FIG. 1 is a graphical representation of a device for inspecting a component. The graphical representation is an elevation view of a device 100. The device 100 can have an inspection platform (platform) 102. The platform 102 can be a stationary, stable platform to support a component 110 to be inspected (e.g., inspected component). The component 110 can be a device or portion of a device that is to be inspected. In some embodiments, the component 110 can be a chipset, an integrated circuit, a printed circuit board (PCB), or other electrical or electronic device to be inspected and analyzed.

The device 100 can have an emitter 120. In some embodiments, the emitter 120 can be an EM emitter, such as an x-ray emitter, a gamma ray emitter, or other type of EM radiation used for inspection of the component 110. The emitter 120 can be disposed on a first side (e.g., below) the platform 102. The emitter 120 can transmit an inspection beam 122 toward the component 110. The inspection beam 122 can be a shortwave light beam used for inspection. For example, the inspection beam can be a beam of X-ray radiation as needed to inspect the component 110. The inspection beam 122 can penetrate the platform 102 and the component 110 to provide information about the composition of the component 110. For example, the inspection beam 122 can provide information regarding the integrity of a weld within a circuit on a PCB.

In some other examples the inspection beam 122 can also be used for inspection of medical equipment (e.g., a pacemaker) or inspection of internal mechanical components (e.g., fractures within a car engine). The inspection beam 122 can also be used for determination of material composition. The inspection beam 122 can allow the device 100 for use in density analysis, crack or void analysis in various types of casting, and non-destructive inspection (NDI) techniques. In some other examples, EM radiation with wavelengths shorter than X-rays, such as, for example, gamma ray radiation can be useful when conducting elemental composition analysis, also known as X-ray fluorescence. Gamma ray inspection can allow determination of the purity of certain metals (e.g., gold), gems and the like, to inspect the elements that form a given substance. It is possible to use such shorter wavelengths in the inspection beam 122, or other non-destructive/non-intrusive options, however that may drive other safety requirements such as a thicker lead lining around the device 100, for example.

The inspection beam 122 can have a beam spread angle 124 (β). The beam spread angle 124 can represent the emitter beam angle or beam divergence of the inspection beam 122.

In some embodiments, the emitter 120 can have at least two degrees of freedom and move in an X axis and a Y axis. The X axis may be referred to herein as the abscissa axis and the Y axis can be referred to herein as the ordinate axis. Thus, in such an embodiment, the emitter 120 can move in the X-Y plane parallel to the platform 102 (e.g., horizontally and in and out of the page). The emitter 120 can also have a third degree of freedom to further move in a Z axis, or applicate axis, to increase or decrease a distance 104 from the bottom of the platform 102. Movement in the Z axis for the emitter 120 can, for example, accommodate a zoom capability of the device 100 allowing an operator to view the component 110 in greater (or lesser) detail as needed. In some embodiments, the distance 104 can be relatively small. For example, the distance 104 can be less than 10 millimeters. Accordingly, FIG. 1 and the other figures described herein may not be drawn to scale for illustrative purposes.

The device 100 can also have a detector 130. The detector 130 can be positioned on a second side of (e.g., above) the platform 102. The detector 130 can receive portions of the inspection beam 122 that penetrate the component 110. The detector 130 can then deliver information related to the composition of the component 110 to a controller for display and analysis (described below). The detector 130 can generally be oriented such that a face, or detector plane 131 of the detector 130 is orthogonal to the inspection beam 122.

The detector 130 can translate in the X, Y, and Z axes. The detector 130 can also articulate (e.g., rotate) about the X and Y axes. This movement capability is illustrated using the X, Y, Z axes extending through the detector 130 and the curved arrows about X and Y axes. Therefore, the detector 130 can have five degrees of freedom and move along an area described by a spherical cap or spherical dome (see FIG. 4) relative to the platform 102 and the emitter 120. As used herein, a spherical cap or dome is the region of a sphere which lies above a given plane. In this figure, only two dimensions of an arc within the spherical dome are shown in the Y-Z plane. Movement of the detector 130 in the Y-Z plane through a range of motion 138 is indicated with an arrow 136.

The detector 130 is shown in three positions 132, labeled position 132*a*, position 132*b*, and position 132*c*. The position 132*a* is positioned directly above the emitter 120 at a reference point 134, located in three dimensions at coordinates (X,Y,ρ), where ρ is the radial distance from a center point 112 to the detector 130. As used herein, the center point 112 is used to refer to a point of interest, or inspection point, on the component 110. As used herein, the reference point 134 is a point in space aligned with a point of interest (e.g., inspection point/center point 112) on the component 110. The detector 130 can translate in the X, Y, and Z axes in coordination with the emitter 120 to establish the reference point 134 directly above the emitter 120 at the same X,Y coordinates. The X,Y coordinates of the emitter 120 and the detector 130 can then be the same as the center point 112 (e.g., vertically aligned). The center point 112 can represent, for example, a point of interest on the component 110.

In some embodiments, the emitter 120 and the detector 130 can move in unison along the X,Y axes to establish a different reference point 134, for example, over a second center point 114 or a third center point 116. Accordingly, the X,Y coordinates of the reference point 134 can be the same as the center point 112 (or, e.g., the second center point 114 and the third center point 116).

Once the reference point 134 is established, the detector 130 can translate in three dimensions (X, Y, and Z axes) and articulate in two dimensions (rotation angles A and B) in order to receive the inspection beam 122 at the desired angle and location in order to inspect the component 110. This provides five degrees of freedom of the detector 130. The detector 130 can move within the spherical cap or spherical dome (see FIG. 4) to change or skew the view of the component as needed. Two of the three dimensions of this movement are shown by a range of motion 138 (and direction 136) at a distance 139. The distance 139 is the dimension (ρ) defined by the distance between the center point 112 (and e.g., the component 110), and the Z coordinate of reference point 134. The distance 139 (ρ) can remain fixed once the center point 112 (and, e.g., the reference point 134) is established for a given inspection routine. In some embodiments, the spherical cap that represents the extent of the three dimensional motion of the detector 130 comprises 30 to 45 degrees to any side of the reference point 134, relative to rotation from the center point 112, for example. A three-dimensional representation of the spherical cap is described in connection with FIG. 4.

Figure 4:
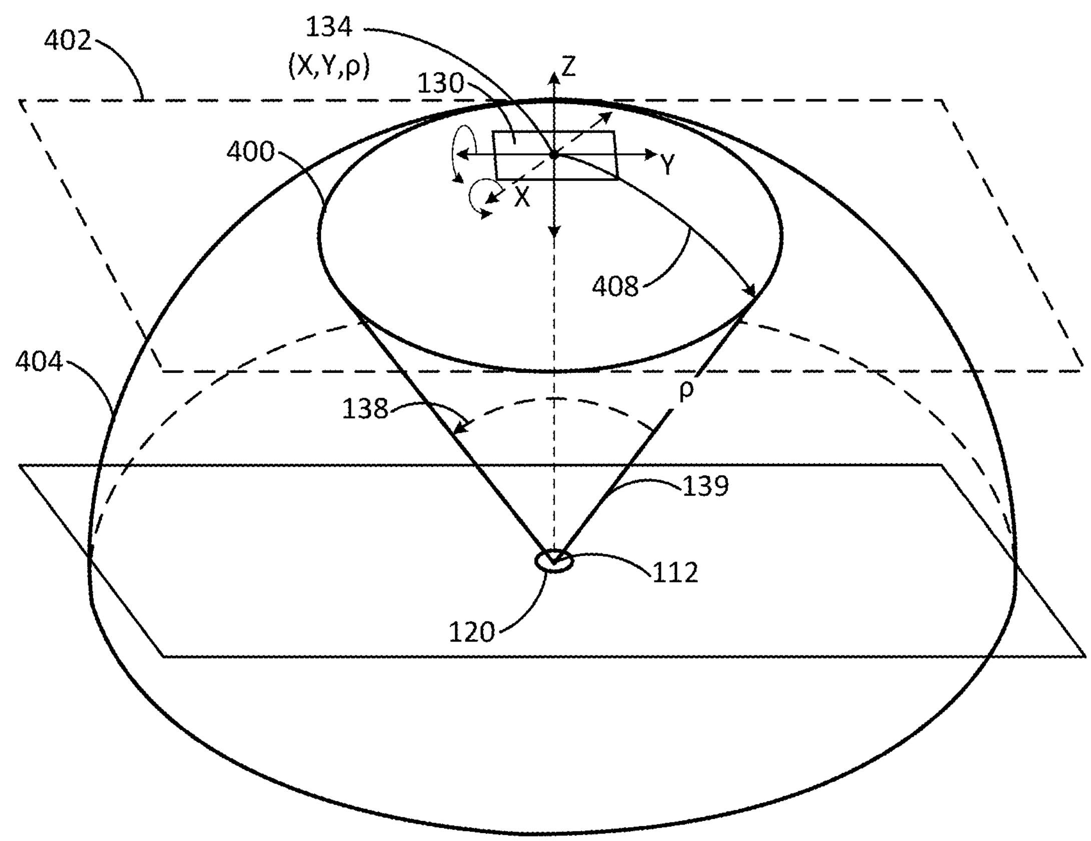
FIG. 4 is a graphical representation of movement of the device of FIG. 1.

The range of motion 138 (*a*) can describe a maximum angular movement of the detector 130 within the spherical dome (FIG. 4). The range of motion 138 can further be similar to the beam spread angle 124 given the relatively short distance 104 between the emitter 120 and the platform 102. Accordingly, in practice, the beam spread angle 124 and the range of motion 138 can be nearly equal.

As shown, the detector 130 at the position 132*b* is rotated away from the reference point 134 to the left, translated in the Y and Z axes, while rotated counterclockwise "A" degrees (e.g., angle A) about the X axis. The detector 130 in the position 132*c* is shown translated to the right in the Y axis, into the page in the X axis, down in the Z axis, rotated clockwise about the X axis and rotated away B degrees (e.g., angle B) in the Y axis from the reference point 134. The five degrees of freedom provided the detector 130 can allow increased flexibility of inspecting the component 110. Each of the positions 132*a*, 132*b*, 132*c* have the same distance 139 (ρ), or radius from the center point 112.

The movement (e.g., translation and rotation) of the detector 130 can also be described in terms of an articulation angle 133, within the range of motion 138. The articulation angle 133 is shown for the position 132*c*, however a similar angle is also used to described the position 132*b*. The articulation angle 133 can be used in calculations for the position 132 and can be adjusted by the user, as described below.

Some inspection systems can allow inspection of a component from various angles. In some examples, the detector 130 can be mounted in a goniometer to provide such a function. A goniometer or goniometric stage is a device used to rotate an object precisely, within a small angular range, about a fixed point in space. In some examples, a goniometer can be used to measure the angles between the faces of crystals. Goniometers can be implemented in an inspection (e.g., X-ray inspection) scenario by mounting a detector (e.g. the detector 130) on the goniometer for precise selection of viewing angles. A goniometer can have an elaborate, hemispherical detector structure overlying an inspection platform. A purpose of a goniometer in x-ray inspection applications is to provide a track upon which the detector can travel. This can further offer a fixed distance from a centralized inspection point on, for example, the platform 102. The use of a fixed, physical goniometer in an x-ray inspection system can require a large footprint for the machine in order to accommodate the size and range of detector travel. Some systems can further have a moving emitter and a moving inspection platform (e.g., the platform 102) with a stationary detector. This can allow precise control of emitter/detector positioning with respect to the component. However, allowing both the emitter and inspection platform to move concurrently can present a risk of contact between the emitter and platform, causing damage to the system. Accordingly, elaborate and complex movement control systems can be required in some goniometers.

The device 100 can provide a similar function to a much larger goniometer while minimizing size, footprint, cost, and complexity. Through various methods using, for example, spherical equations, the device 100 can provide movement and viewing angles not previously possible without a goniometer.

Figure 2:
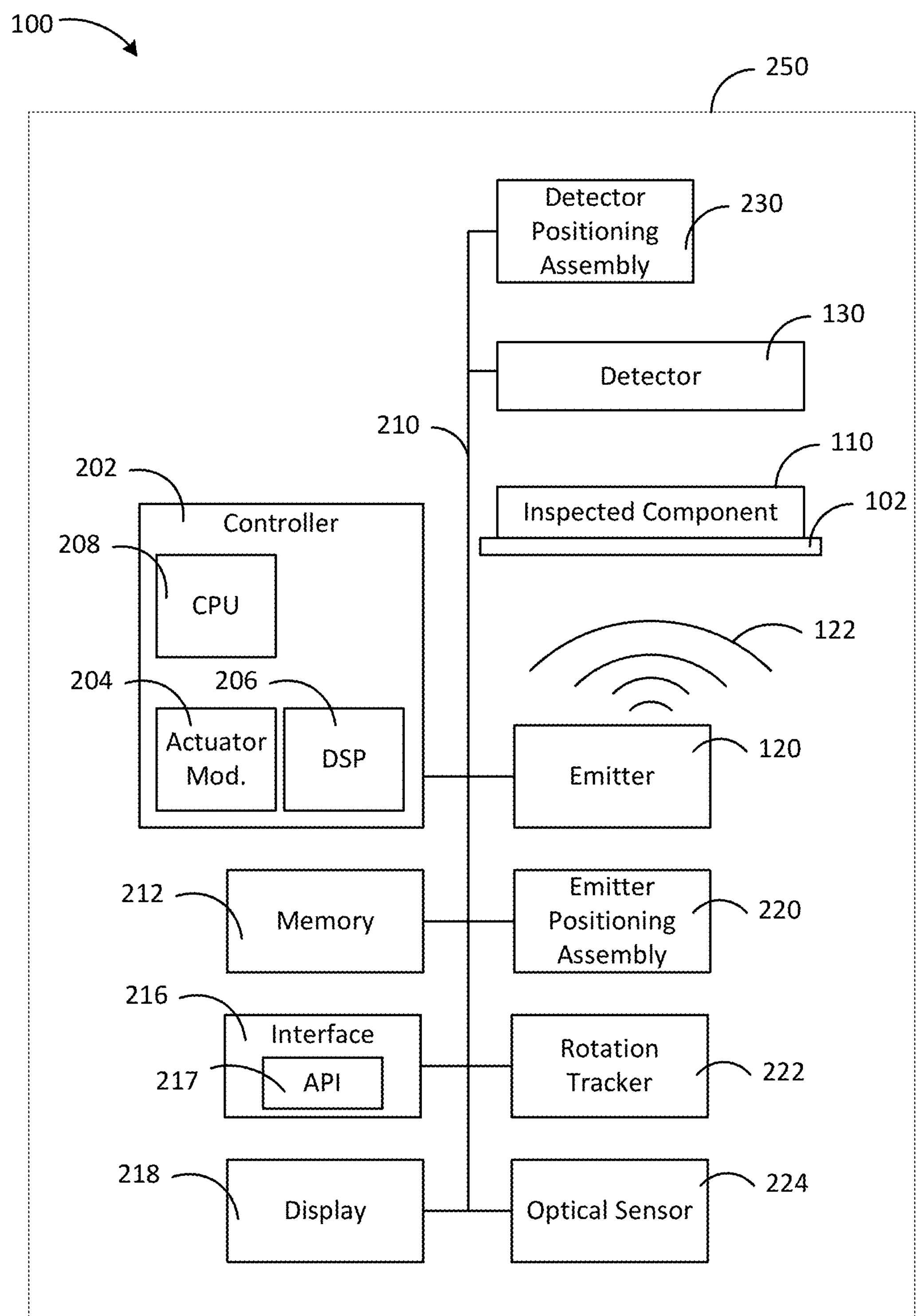
FIG. 2 is a functional block diagram of the device of FIG. 1.

FIG. 2 is a functional block diagram of the device of FIG. 1. The device 100 can have a controller 202. The controller 202 can have a central processing unit (CPU) 208. The CPU 208 can have one or more processors or microprocessors. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the CPU 208 and/or the controller 202. For example, the controller 202 can also have an actuator module 204 for communicating commands to one or more actuators for moving (e.g., translating and articulating the emitter 120 and the detector 130). The actuator module 204 in conjunction with the CPU 208 can further control power output of the emitter 120. In some examples, the actuator module 204 in conjunction with the CPU 208 can also control sensitivity or gain of the detector 130. The controller 202 can further have a digital signal processor (DSP) 206 for processing communications or other data to and from the emitter 120 and the detector 130.

The controller 202 can be operably coupled to a communications bus 210. The communications bus 210 may include a data channel for facilitating information transfer between storage and other peripheral components of the device 100. In an embodiment, the communications bus 210 can facilitate the exchange of information between the controller 202 and the emitter 120 or between the detector 130 and the controller 202, for example. The communications bus 210 can also facilitate communications among the various components of the device 100, for example.

The communications bus 210 may further provide a set of signals used for communication with the controller 202, including a data bus, address bus, and control bus for the actuator module 204, for example.

The device 100 can also have a memory 212 coupled to the communications bus 210. The memory 212 can provide storage of instructions and data for programs executed by the controller 202. In some embodiments the memory 212 can be a semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The memory 212 can also include an internal memory and/or a removable medium, for example a floppy disk drive, a magnetic tape drive, a compact disc ("CD") drive, a digital versatile disc ("DVD") drive, etc. Such removable media can include, for example, a floppy disk, magnetic tape, CD, DVD, SD card, etc. Such can be non-transitory computer readable medium having stored thereon computer executable code (i.e., software) and/or data. The computer software or data stored on the memory 212 can be read into the device 100 for execution by controller 202.

In some other embodiments, the memory 212 can include other similar means for allowing computer programs or other data or instructions to be loaded into the device 100. Such means may include, for example, an external storage medium coupled to an interface 216 (described below). Examples of an external storage medium may include an external hard disk drive or an external optical drive, or and external magneto-optical drive.

Other examples of memory devices use in the memory 212 can include semiconductor-based memory such as programmable read-only memory ("PROM"), erasable programmable read-only memory ("EPROM"), electrically erasable read-only memory ("EEPROM"), or flash memory (block oriented memory similar to EEPROM).

The device 100 can also have an interface 216. The Interface 216 can facilitate input from and output to external devices for transfer of data. For example the interface 216 can have one or more of hardware, firmware, and/or software configured to receive input from a keyboard, mouse, or other input device such as, for example, a touchscreen display, and may provide output to a display (e.g., a display 218). The interface 216 is operable to facilitate input from and output to various alternative types of human interface and machine interface devices alike. The interface 216 can make use of wired or wireless connections to such external input and output devices.

The interface 216 can further allow external communications. For example, the interface 216 can allow software and data to be transferred between device 100 and external devices (e.g. printers), networks (not shown), or other information sources. For example, computer software or executable code may be transferred to the device 100 from a network server via the interface 216 via wired or wireless connections. Examples of the interface 216 can include one or more antennas, a modem, a network interface card ("NIC"), a wireless data card, a communications port, a PCMCIA slot and card, a parallel port, a serial port, an infrared interface, and an IEEE 1394 fire-wire, to name but a few.

The interface 216 can implement industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

The interface 216 can further have an application-program interface (API) 217. In some embodiments, the API 217 can represent a plurality of APIs. The API 217 can provide the ability to trivially replace certain components of the inspection system for various custom applications. Many systems are tightly coupled to the originally selected components and neither the physical system nor the control software can be cost-effectively modified to support a wide array of applications. The API 217 can have one or more of a motion control API, an emitter API, a detector API, and an optical camera API.

The Motion Control API is used for controlling the motors or actuators responsible for moving the various components within the system. The emitter API is used to control the light- or EM radiation-emitting component (e.g., power, current, etc.) The detector API is used for controlling the detector (e.g., the detector 130) for the specific light wavelength generated by the emitter (e.g., the emitter 120) being used. The detector API can also be used for controlling aspects of the device 100 such as, for example, frame rate (e.g., the speed of transmission of frames), image offsets, grayscale adjustments, etc. The optical camera API is used for controlling any optical cameras (e.g., an optical sensor 224) that might be required or used within the system for navigation or visual inspection. The optical camera API can also be used for controlling aspects of the optical sensor 224 such as lens focus, aperture, and exposure, among other things.

The display 218 can be coupled to the communications bus 210. The display 218 can provide a visual output of the inspection beam 122 detected by the detector 130. For example, the display 218 can provide a visual representation or output an X-ray image of the component 110. The display 218 can further provide a touchscreen input for manipulating the image and directing the inspection beam 122. The display 218 can function with the interface 216 as a user interface for manipulating and controlling the device 100.

The device 100 can have an emitter positioning system 220 coupled to the communications bus 210. The emitter positioning system 220 can be one or more actuators or motors and associated hardware (e.g., electric or electromechanical motors) for moving the emitter 120. For example, the emitter positioning system 220 can have a series of tracks in each of the X,Y,Z axes in addition to rotating actuators, for example. The emitter positioning system 220 can receive movement commands from the controller 202 or from the user input via the display 218, for example. The emitter positioning system 220 can move the emitter 120 in the X, Y, and Z axes as described herein.

The device 100 can also have a detector positioning system 230 coupled to the communications bus 210. The detector positioning system 230 can be one or more actuators or motors and associated hardware (e.g., electric or electro-mechanical motors) for moving the detector 130. For example, the detector positioning system 230 can have a series of tracks in each of the X,Y,Z axes in addition to rotating actuators about the X and Y axes, for example. The detector positioning system 230 can receive movement commands from the controller 202 or from the user input via the display 218, for example. The detector positioning system 230 can then move (e.g., translate or articulate) the detector 130 as needed to provide a desired visual output of the component 110.

The device 100 can have a rotation tracker 222. The rotation tracker 222 can be coupled to the communications bus 210. The rotation tracker 222 can track the position of the emitter 120 and the detector 130 in three dimensions to feed position information back to the controller 202. The position and angle information can be provided on the display 218.

The optical sensor 224 can be coupled to the communications bus 210. The optical sensor 224 can have a similar view of the component 110 as the detector 130. In some embodiments, the optical sensor 224 and the detector 130 can have substantially identical fields of view so as to provide a visual indication of the portion of the component 110 to be inspected with the inspection beam 122. This can allow a user to appropriately position the emitter 120 and the detector 130. In some implementations, a field of view of the detector 130 is approximately coaxial with that of the optical sensor 224. In some other implementations, the detector 130 and optical sensor 224 can be mounted to a rotatable mechanism that provides the similar fields of view. For example, the optical sensor 224 and the detector 130 can be disposed on different sides of a rotatable assembly. Accordingly, when a visible light view of the component 110 is needed, the optical sensor 224 can be rotated into place. Conversely, when an inspection image (e.g., an X-ray image) is needed, the optical sensor 224 is rotated out of position as the detector 130 rotates into position.

In some embodiments, the component 110 can be placed on the platform 102. A visual indication of a portion of the component 110 to be inspected can be shown via the optical sensor 224 on the display 218. Touch input can be received from the display 218 indicating a desired position for inspection. The position input is received by the controller 202 and the actuator module 204 can command the movement of the emitter positioning system 220 and the detector positioning system 230. In some examples, the actuator module 204 can be based on certain commands or feedback from the rotation tracker 222.

The device 100 can further have an exterior cover 250. The exterior cover 250 can have a liner that can prevent spurious EM transmissions from escaping to the surrounding environment. For example, the exterior cover 250 can define a cavity surrounding the other components (e.g., the component 110, the emitter 120, and the detector 130). The exterior cover 250 can further be lined with lead, metallic mesh, or other material to minimize the escape of the inspection beam 122. A lead-lined exterior cover 250 may be impermeable to an inspection beam 122 using x-ray radiation, for example.

Figure 3:
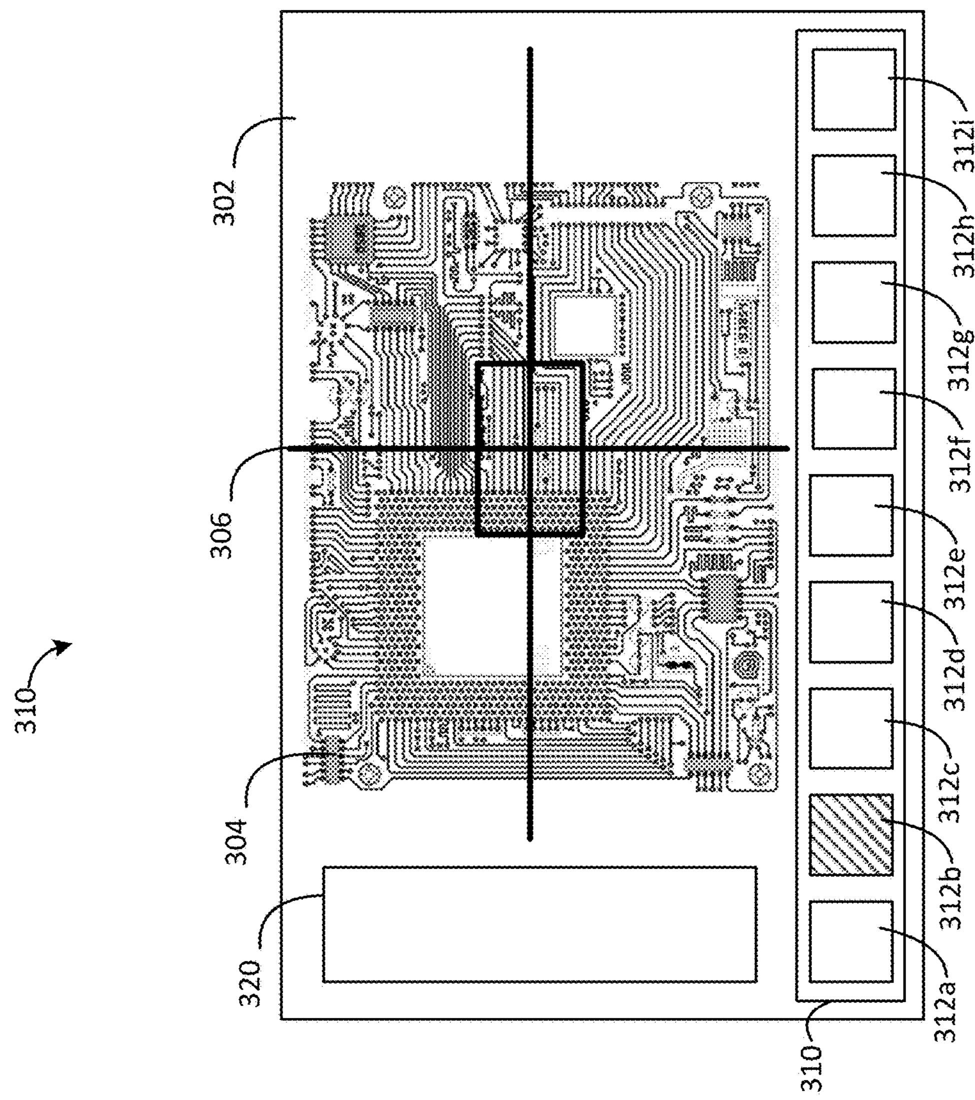
FIG. 3 is a graphical representation of a user interface for use with the device of FIG. 1.

FIG. 3 is a graphical representation of a user interface for use with the device of FIG. 1. A user interface (UI) 300 can combine, for example, one or more of the capabilities and functions of the interface 216 and the display 218 (FIG. 2). The UI 300 can provide a touch-enabled display for control of the device 100. The UI 300 can display information related to inspection of the component 110, position of the emitter 120, angle and position of the detector 130, and various other tasks and analysis-related functions of the device 100. In some examples, the UI 300, and the device 100 more generally, combines the features of a viewing application, motion control of the emitter 120 and the detector 130, and power control of the emitter 120 into a single device. The UI 300 can be implemented in, for example, a touchscreen monitor, wireless-enabled tablet, or other similar system. This can provide a user with a cohesive and intuitive interface for full control of the device 100.

The UI 300 can have an integrated touch-driven interface for machine control (e.g., control of the emitter 120 and the detector 130) and imaging of the component 110. The UI 300 can be a programmable display that provides flexibility in what functions, buttons, or other input options are provided and where, on the UI 300 (e.g., the display 218). This exemplary interface of the UI 300 provides an operator with a simple and intuitive way to interact and control the device 100.

The UI 300 can have a touch-based navigation area 302. The touch-based navigation area 302 can receive touch input and enable positioning and manipulation of the emitter 120 and the detector 130. In some embodiments, the optical sensor 224 can provide an image 304 of the component 110 in the touch-based navigation area 302. In some implementations, the images produced by the optical sensor 224 can provide a primary link between the UI 300 and the component 110 being inspected. The device 100 (e.g., the controller 202) can create a live, or real time map of the component 110. Such a map can be created upon initialization of the device 100 or loading of the component 110 (within e.g., the cover 250 or the cabinet 802 of FIG. 8), for example. The map can comprise the image formed by the optical sensor 224 that is then calibrated to allow exact one-to-one (1:1) scaled motion positioning for the emitter 120 and the detector 130. For example, the image seen displayed on the touch-based navigation area 302 (e.g., the display 218) may depict exact positional references of the component 110. This provides a significant advantage to the operator in making real-time selection of portions of the component 110 to inspect.

The UI 300 can have an indicator 306 showing a portion of the component of interest. A user can drag the indicator 306, shown here as a crosshairs, to an area of interest on the component 110. The indicator 306, and the touch-based navigation area 302 in general, can allow the operator to define a region of interest within the component 110. The controller 202 can interpolate the zoom level (of the display 218) based on an aspect ratio of the selected region using the indicator 306, for example. The aspect ratio and center of selected region within the touch-based navigation area 302 can allow the controller 202 to precisely command the emitter positioning system 220 and the detector positioning system 230 to the necessary three dimensional position 132 (FIG. 1). In other implementations, the indicator 306 can allow the operator to manipulate the selected region after it has been initially drawn or defined. The device 100 can then control the movement of the emitter 120 and the detector 130 to provide an image (e.g., the image 304) of the component using the inspection beam 122. The image 304 shown in FIG. 3 can be representative of, for example, an x-ray inspection image of the component 110. The image 304 can also be representative of a visible light image from the optical sensor 224.

The UI 300 can receive the touch-based commands, transmit them to the controller 202 and in conjunction with the actuator module 204, the emitter positioning system 220 and the detector positioning system 230, navigate the emitter

120 and the detector 130 to the desired location. This can eliminate the need for other input devices, such as, for example, a joystick for manually positioning the emitter 120, the detector 130, and optical sensor 224 to arrive at the desired view. The operator is then able to view and inspect the component 110 at the desired location on the same display (e.g., the display 218) having the controls.

The display shown in FIG. 3 can be referred to herein as a high level display, providing a plan view of the component 110 and a plurality of high level functions, such as motion programming (macro) and motion control, image analysis, inserting annotations on the image, detection angle manipulation, configuration and control of the inspection beam 122, live view of inspection images (e.g., x-ray images), and documentation view, among other options. The UI 300 can have a capabilities dock 310 with a plurality of high level functions 312 distributed on the UI 300 implementing a context-driven user interface. The capabilities dock 310 and the high level functions 312 can be overlaid on the touch-based navigation area 302 as well. The capabilities dock 310 can show all the high-level capabilities or features of the system (e.g., image capture, image analysis, tilt, movement, etc.).

In the embodiment shown, nine high level functions 312 are shown distributed along the bottom of the touch-based navigation area 302. The nine high level functions 312 are labeled 312*a*, 312*b*, 312*c*, 312*d*, 312*e*, 312*f*, 312*g*, 312*h*, and 312*i* (collectively, high level functions 312). The position and number of the high level functions 312 within the UI 300 should not be considered limiting. The high level functions 312, or any other function or display/subdisplay for that matter, can be positioned as needed on the UI 300.

In one example, the high level function 312*b* (shown with cross-hatching) can be an image manipulation task capability. Once selected, a contextual display 320 associated with the high level function 312*b* can be shown. The contextual display 320 is shown on the left of the UI 300, but can be positioned anywhere on the touch-based navigation area 302. When a particular high level function 312 is selected or enabled, the options/actions associated with that function are then displayed in the contextual display 320 to the operator. The contextual display 320 can then display applicable options/actions relevant to the active high level function 312. By simplifying the possible interactions for the operator based on the context of the capability they have enabled, it allows for a much more intuitive user experience, thereby increasing the efficiency of the operator. The context-driven user interface addresses the issue of overwhelming the operator with all the possible functions of the system in the traditional menus and buttons layout.

FIG. 4 is a graphical representation of movement of the device of FIG. 1. As noted above, the detector 130 is operable to move in a curved plane or path described by a surface of spherical dome 400, the top of which is centered on and coincident with the reference point 134. The spherical dome 400 is a spherical cap, described by the intersection of a plane 402 with a hemisphere 404. The spherical dome 400 can also be described as the top of a cone-shaped section of the hemisphere 404 described by the range of motion 138 and the distance 139 rotated about the Z axis. The hemisphere 404, on the other hand, can represent, for example, the range of motion of a goniometer. In some embodiments, the spherical dome 400 can extend from the reference point 134 in an arc 408 and revolved about the Z axis. In some embodiments the arc 408 can be 15-45 degrees. In some other embodiments, the arc 408 can be 30 degrees. In some other embodiments, the arc can be 0 to one-half the emitter beam angle (e.g., the beam spread angle 124). For example, in the illustrated examples of FIG. 1 and FIG. 4 the beam spread angle 124 (e.g., emitter beam angle) can be approximately 60 degrees. By extension then, the arc 408 can be 0-30 degrees. The emitter 120 can have a wider or narrower inspection beam 122 (e.g., with a different beam spread angle 124), but this concept remains the same despite the angular values.

The region defined by the spherical dome 400 represents the area where the detector 130 can move (e.g., a 60 degree range, rotated about the Z axis). The UI 300 can display a plan view of the component 110 (e.g., FIG. 3) and a desired area for inspection can be selected via a touch input on the display 218, by the operator, for example. The controller 202 can then determine an appropriate reference point 134. The operator can further select a position within the spherical dome 400. The controller 202 can then calculate angles from the center point 112 to the selected position 132, based on the distance 139. The controller 202 can then command the emitter positioning system 220 and the detector positioning system 230 to move the emitter 120 and the detector 130 to the appropriate location for inspection of the component 110. The UI 300 can further provide high level functions 312 and contextual display 320 (e.g., contextual controls) to, for example, adjust the detector articulation angle 133 to move the detector 130 about the surface of the spherical dome 400 for fine-tuned movements and/or more precise views of the component 110. In some examples, a jog feature can be activated once the operator has selected a region of interest and the X-ray view of the component 110 has been activated. Once in this view, the operator will no longer have the plan view, optical component (e.g., the component 110) map to navigate between desired views (from e.g., the position 132*a* to the position 132*b* or the position 132*c*). Therefore, the operator can use the jog function to directly manipulate views using the X-ray image by manually jogging the appropriate axes (via, e.g. the emitter positioning system 220 and the detector positioning system 230). The jog feature can allow the emitter 120 and the detector 130 to move in unison to maintain the same aspect or view at a different inspection point. For example, the inspection point can be moved from the center point 112 to the second center point 114 while maintaining the same angular or skewed view of the component (e.g., from the position 132*c*).

The position of the detector 130 within the spherical dome can be calculated by spherical equations. Accordingly, the device 100 can achieve the five space movement that can produce certain viewing angles, such as skewed or angular views that were previously only possible using a goniometer.

Figure 5:
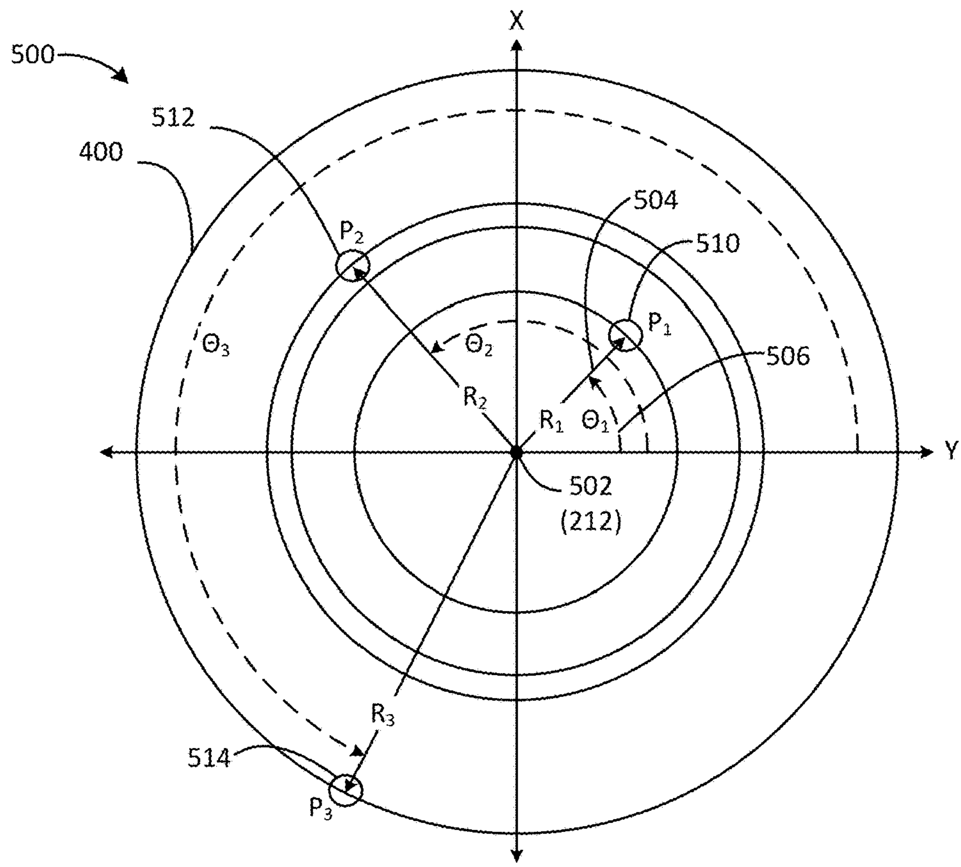
FIG. 5 is a diagram of a two dimensional plan view of the spherical dome of FIG. 1 and FIG. 4.

FIG. 5 is a diagram of a two dimensional plan view of the spherical dome of FIG. 1 and FIG. 4. A display 500 depicts three points $P_1$ 510, $P_2$ 512, and $P_3$ 514 that the user may select. The skilled person should appreciate that the location of the three points is not limiting to the disclosure. Each of the points $P_1$ 510, $P_2$ 512, and $P_3$ 514 represents different locations to which the detector 130 can be moved along the spherical dome 400. Each of the points $P_1$ 510, $P_2$ 512, and $P_3$ 514 can be used to provide a different view of the component 110. For example, the UI 300 (e.g., the display 218) can present such a two dimensional representation (e.g., the display 500) on the touch-based navigation area 302.

In a first approach to positioning the detector 130, a specific position such as for example, one of the points $P_1$, $P_2$, or $P_3$, can be selected, via a manual or touch input on the UI 300. The controller 202 can then interpolate necessary information to command the emitter positioning system 220 and the detector positioning system 230. The display 500 can have a display center 502. In some examples, the UI 300 can present the display in a plan view, where the display center 502 is coincident with the center point 112 (and the reference point 134) in the X and Y axes. That is, the center point 112 and the display center have the same <X,Y> coordinates, but are separated by the distance 139 (FIG. 1) in the Z axis. The distance 139 also represents the fixed distance between the detector and the center point 112 of the platform 102.

The points $P_1$ 510, $P_2$ 512, and $P_3$ 514 can each have a radial distance (R) from the display center 502 (coincident in the X and Y planes with the center point 112). For example, the point $P_1$ is a distance ($R_1$) 504 from the display center 502 and an angular position ($\theta_1$) 506 relative to the positive X axis. Because the spherical dome 400 is a curved surface, the radial component $R_1$ (e.g., the distance 504) can be a linear scalar having a value representing an angular value Φ (phi), where Φ is an angle with respect to the Z axis (the Z axis in this view extends into and out of the page at the display center 502). The angle Φ is positive in the clockwise direction when viewing the X-axis of a standard X,Y,Z coordinate system. The angle Φ helps determine the sweep angles in X-Z plane and the Y-Z plane. In an embodiment using the articulation angle 133 equal to 30 degrees, the radial component $R_1$ can have a value from 0-30, equivalent to the detector articulation angle 133 (FIG. 1). The position of the detector 130 at the point 510 $P_1$ (or any other point in three dimensional Cartesian space) can be represented in Cartesian coordinate space using the following equation:

$$x^2+y^2+z^2=\rho^2 \quad (1)$$

Each of the values x, y, and z are units in distance from the origin (e.g., the center point 112). Using the standard spherical coordinate space, Equation (1) can therefore be represented using the spherical components (e.g., the angular position 506 $\theta_1$ and the detector articulation angle 133 Φ) and the distance 139 (ρ) representing the fixed distance 139 of the curved plane of the spherical dome 400 from the component 110 at the center point 112. Accordingly the following equations are used:

$$X=\rho \sin \theta \cdot \cos \Phi \quad (2)$$

$$Y=\rho \sin \theta \cdot \cos \Phi \quad (3)$$

$$Z=\rho \cos \theta \quad (4)$$

The controller 202 can then provide a three dimensional coordinate for the point 510 ($P_1$) to the detector positioning system 230 to appropriately position the detector 130. The point 512 ($P_2$) and the point 514 ($P_3$) can be calculated using the same functions. A benefit of the first approach using the spherical coordinate extrapolation from the polar coordinate representation is a quick method of positioning the detector 130 by selecting a position (e.g., the position 132) with reference to the display center 502. This can also eliminate the need to manually jog the angular position of the detector 130 individually in two axes.

Figure 6:
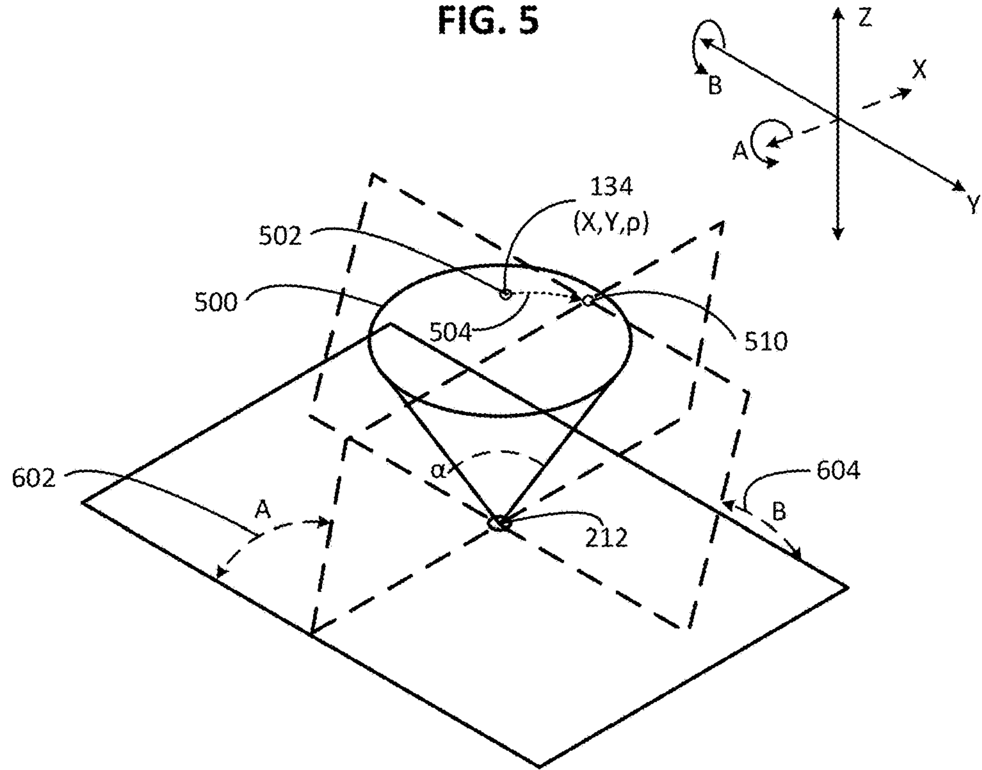
FIG. 6 is a graphical representation of the three dimensional positioning of the detector of FIG. 1.

FIG. 6 is a graphical representation of the three dimensional positioning of the detector of FIG. 1. The detector 130 can be positioned using an angle A 602 and an angle B 604 through matrix transforms. During inspection of the component 110, the detection surface of the detector 130 should be orthogonal to the inspection beam. The face of the detector 130 is pointed directly at (e.g., orthogonal to) the center point 112 and tangent to the spherical dome 400. Advantageously, this can provide a skewed view or angular view relative to the point of interest (e.g., the center point 112). In order to ensure the surface of the detector 130 is tangent to the spherical surface (e.g., the spherical dome 400) and orthogonal to the inspection beam 122, an abscissa deflection angle 602 (A) and an ordinate deflection angle 604 (B) can be derived using the values of the (X, Y, Z) coordinates of, for example, the point 510 ($P_1$) using ARCTAN functions:

$$A=\arctan(Z/X) \quad (5)$$

$$B=\arctan(Z/Y) \quad (6)$$

Equation (5) and equation (6) can be used to derive any position about the dome 400.

In a second approach to positioning, the detector 130 can be positioned at a desired position (e.g., the point 510) in three dimensional space using the abscissa deflection angle 602 (A) and the ordinate deflection angle 604 (B) relative to the center point 112 (e.g., <0,0,0>) as the known variables.

In this second implementation method, the controller 202 can position the detector 130 based on the rotation of the detector 130 with respect to each of the X axis or Y axis.

Beginning with the display center 502 or the reference point 134 (FIG. 1), which is the distance 139 away from the center point 112 at coordinates <0,0,ρ>, a rotation matrix can be applied relative to both the X and Y axes. The reference point 134 is where the detector is ρ units directly above the center point 112. This point is rotated about the X axis by "A" degrees. Then the resulting transformed point can be rotated about the Y axis by "B" degrees. The final, dual-axis rotation can be translated to the desired three dimensional point 510 (e.g., the position $P_1$) by a linear <X,Y> shift to the location of the emitter 120, in the X and Y axes.

An advantage of this approach is that a user can jog the detector 130 using, for example, directional arrows on the UI 300, for fine-tuning the position of the detector 130 while giving a 'sense of motion direction.' This is a benefit because when observing a highly magnified inspection image (e.g., an x-ray image), it is easy for an observer to lose their frame of reference.

A third approach can combine both the first method and the second method. For example, a desired inspection position (e.g., one of the positions 132) can be selected via the touch-based navigation area 302 (e.g., the display 218). Then the second method can be used to fine tune the orientation of the detector 130 with respect to both angle A and angle B.

Figure 7:
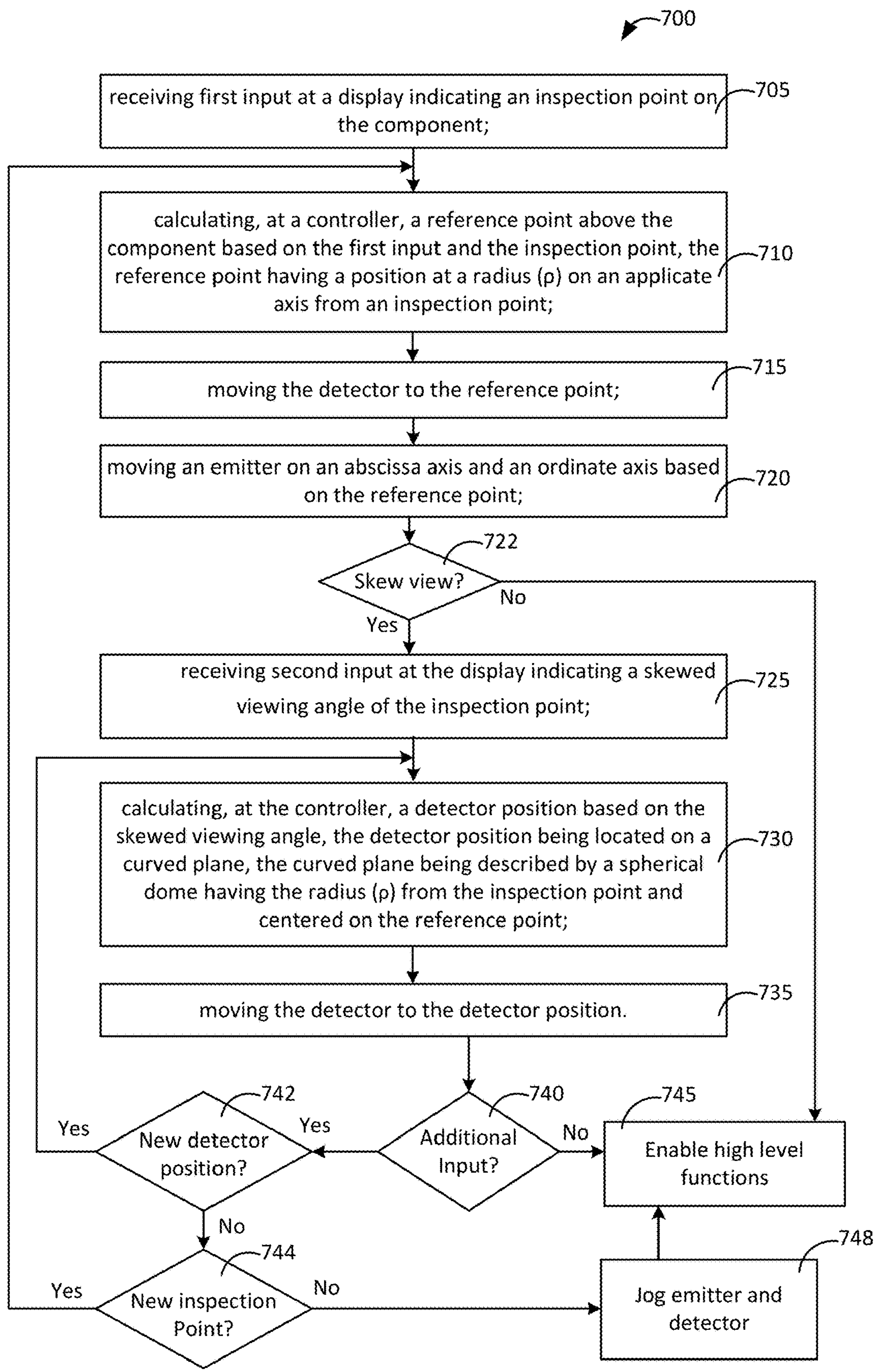
FIG. 7 is a flowchart of a method for inspecting a component.

FIG. 7 is a flowchart of a method for inspecting a component. A method 700 can include using the device 100 for inspecting the component 110, for example. At block 705 the controller 202 can receive an input (e.g., a first input) from, for example, the display 218. The display 218 can receive touch-based input indicating an inspection point (e.g., defining the center point 112) on the component 110. The touch-based input can be received on an image of the component 110 provided by the optical sensor 224, for example. The optical sensor 224 and the detector 130 can have a similar field of view of the component 110.

At block 710, the controller 202 can calculate the reference point 134 above the component 110 based on the first input (e.g., the inspection point). As noted above, the reference point 134 can have a position at a radius (ρ) away from the inspection point (e.g., the center point 112) on an applicate axis.

At block 715, the controller 202 can move the detector 130 (using, e.g., the detector positioning system 230) to the reference point 134, above the center point 112 (e.g., the inspection point).

At block 720, the controller 202 can move the emitter 120 on an abscissa axis and an ordinate axis based on the reference point 134. Movement of the emitter 120 can be completed in unison with the detector 130 on the abscissa and ordinate axes to maintain alignment. The emitter 120 can further move in the applicate axis according to zoom requirements. In some implementations, the functions of block 715 and block 720 can be performed simultaneously.

At decision block 722 if another input (e.g., a second input) is received at the display 218 indicating a skewed viewing angle of the inspection point (e.g., the center point 112) the method 700 moves to block 725.

At block 725, the controller 202 can receive the second input at the display 218. The second input can indicate a skewed viewing angle of the inspection point. The skewed viewing angle can be derived from touch-based input on the display 218.

At block 730, the controller 202 can calculate a detector position (e.g., the position 132*a*, 132*c*) based on the second input from block 725. The second input can indicate a (skewed) viewing angle of the inspection point. The detector position can be located on a curved plane (e.g., the spherical dome 400) above the inspection point. As described in connection with FIG. 4, FIG. 5, and FIG. 6, the curved plane can being described by the spherical dome 400 having the radius (ρ) from the inspection point and centered on the reference point 134.

At block 735 the controller 202 can further move the detector 130 to the detector position indicated by the second input.

In some implementations, if additional input can be received at the display 218. The additional input can be, for example, an indication of a new inspection point (e.g., the second center point 114 or the third center point 116) that forces the need to calculate a new reference point 134 and move the emitter 120 and the detector 130. The additional input can also be a change in the viewing angle that modifies the detector position (within the spherical dome 400) determined at block 730. This can be similar to moving the detector 130 from the position 132*b* to the position 132*c*, for example. The additional input can further be a jog function. The jog function can allow the inspection point to change (e.g., the center point 112 to the second center point 114) while maintaining the same viewing angle (e.g., the skewed viewing angle) determined at block 730. This provides the same viewing angle calculated at block 730, but allows manipulation of the inspection point.

If at decision block 740, no additional inputs are received, then the controller 202 can enable certain other high level functions (e.g., the high level functions 312 described in connection with FIG. 3). The high level functions 312 can provide various tools to analyze inspection images of the component 110, among other functions, If at decision block 740 additional input has been received (by, e.g., the display 218) the method 700 can move to decision block 742. At decision block 742, if a new detector position is indicated in the additional input, the method 700 can return to block 730 to calculate or determine a new detector position (e.g., the position 132*b*, 132*c*) and move the detector 130 accordingly. If at decision block 742 the additional input does not indicate a new detector position, the method 700 can proceed to decision block 744.

At decision block 744, if the additional input from decision block 742 indicates a new inspection point, the method 700 can return to block 710 to recalculate the reference point 134 can move the emitter 120 and the detector 130 as required.

If the additional input is a jog function at decision block 740, (e.g., “No” at decision block 742 and “No” at decision block 744) at block 748, the controller 202 can command the emitter positioning system 220 and the detector positioning system 230 to move the emitter 120 and the detector 130 (respectively) to maintain the same viewing angle at a new inspection point. As noted above, the jog function can allow the inspection point to change (e.g., center point 112 to the second center point 114) while maintaining the same relative position of the emitter 120 and the detector 130.

Similarly, at decision block 722, if no skewed viewing angle is required, the controller 202 can also enable the high level functions 312.

Once the emitter 120 and the detector 130 are at a desired position following the jog function at block 748, the controller 202 can then enable the high level functions 312 at block 745.

Figure 8:
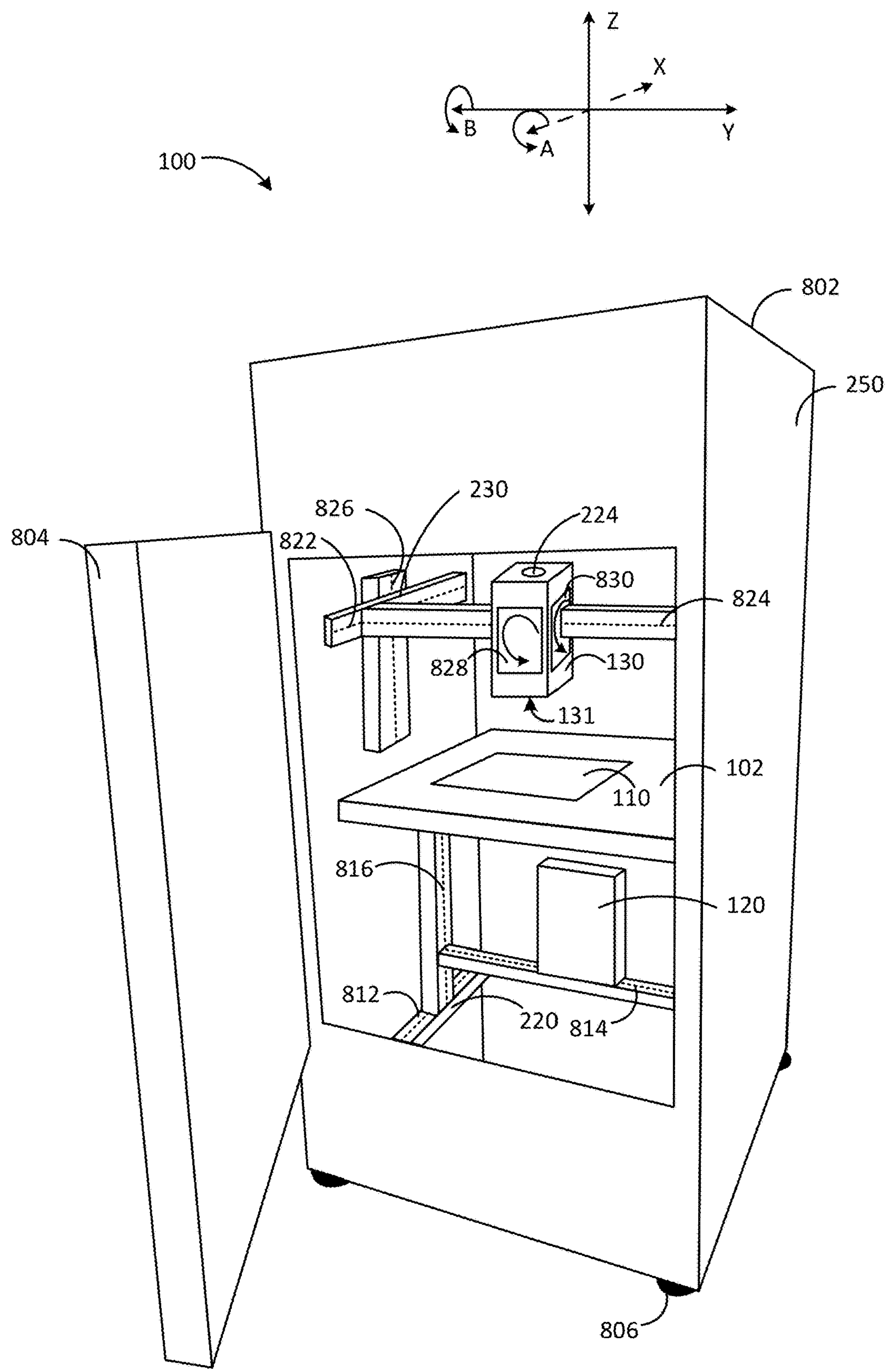
FIG. 8 is a graphical depiction of an embodiment of the device of FIG. 1.

FIG. 8 is a graphical depiction of an embodiment of the device of FIG. 1. The device 100 can have a cabinet 802 having an opening 804. The cabinet 802 and the opening 804 can comprise, or at least similar to, the exterior cover 250 (FIG. 2). The cabinet 802 can be a lead-lined enclosure, for example, to prevent portions of the inspection beam 122 (e.g., EM radiation, X-rays, gamma rays, etc.) from escaping to the surrounding environment. The cabinet 802 can also have a metallic mesh or other materials to minimize the escape of the inspection beam 122. The opening 804 can provide access to the platform 102 for insertion and removal of the component 110. The opening 804 can also be configured as, for example, a hinged door (as shown), a sliding door, a drawer, or similar access point allowing insertion and removal of the component 110. The cabinet 802 can further have wheels 806. The wheels 806 can be casters or other rolling or sliding mechanisms for movement of the device 100.

As shown, the emitter positioning system 220 can have three tracks, sets of tracks, or actuators aligned in the X,Y,Z axes. The emitter positioning system 220 can have an emitter X track 812 aligned with the abscissa (X) axis allowing translation of the emitter 120 in a direction aligned with the X axis.

The emitter positioning system 220 can have an emitter Y track 814 aligned with the ordinate (Y) axis allowing translation of the emitter 120 in a direction aligned with the Y axis.

The emitter positioning system 220 can have an emitter Z track 816 aligned with the applicate (Z) axis allowing translation of the emitter 120 in a direction aligned with the Z axis. The controller 202 can communicate with the emitter positioning system 220 to appropriately move the emitter 120 according to the inspection point (e.g., the center point 112) and other input or commands, as needed.

In some implementations, the emitter positioning system 220 can have complementary tracks for the emitter X track 812 and the emitter Z track 816 on the opposite side of the cabinet 802 that are obscured in this view.

Similarly, the detector positioning system 230 can have three tracks, sets of tracks, or actuators aligned in the X,Y,Z axes. The detector positioning system 230 can have a detector X track 822 aligned with the abscissa (X) axis allowing translation of the detector 130 in a direction aligned with the X axis.

The detector positioning system 230 can have a detector Y track 824 aligned with the ordinate (Y) axis allowing translation of the detector 130 in a direction aligned with the Y axis.

The detector positioning system 230 can have a detector Z track 826 aligned with the applicate (Z) axis allowing translation of the detector 130 in a direction aligned with the Z axis.

The detector positioning system 230 can have a detector X rotation actuator 828 allowing rotation of the detector 130 about the X axis. The detector positioning system 230 can have a detector Y rotation actuator 830 allowing rotation of the detector 130 about the Y axis. The controller 202 can further communicate with the detector positioning system 230 to appropriately move the detector 130 according to, for example, the inspection point (e.g., the center point 112), skewed angle commands (e.g., the second input) or additional input (e.g., the high level functions 312), zoom or jog commands, etc., as needed.

In some implementations, the detector positioning system 230 can have complementary tracks for the detector X track 822 and the detector Z track 826 on the opposite side of the cabinet 802 that are obscured in this view.

As noted above, the optical sensor 224 can also be fitted to the detector 130 or the detector positioning system 230. For example, the optical sensor 224 can be on a different side of the detector 130 than the detector plane 131. In some embodiments, the controller 202 can command the detector positioning system 230 (and more specifically, the detector Y rotation actuator 830, for example) to rotate the detector 130 such that the optical sensor 224 can view the component 110. As shown, the optical sensor 224 is positioned on the detector opposite the detector plane 131. This can allow coaxial views of the component 110 using both the optical sensor 224 and the detector 130. Thus the controller 202 can map the inspection image (e.g., X-ray image) of the component 110 to a visible light image with the same dimensions from the same perspective. This can allow a user to position the inspection point (center point 112) on the visible light image without losing track of orientation of the viewing aspect. Thus an X-ray image or inspection image can have, for example, a one-to-one correlation with the visible light image.

Various embodiments may also be implemented primarily in hardware using, for example, components such as application specific integrated circuits ("ASICs"), or field programmable gate arrays ("FPGAs"). Implementation of a hardware state machine capable of performing the functions described herein can also be apparent to those skilled in the relevant art. Various embodiments may also be implemented using a combination of both hardware and software.

Furthermore, those of skill in the art can appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in any following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

What is claimed is:

1. An x-ray inspection system comprising:

an inspection platform for supporting a component to be inspected;

an x-ray emitter configured to generate an inspection beam and disposed on a first side of the inspection platform;

a detector configured to detect the inspection beam, and disposed on a second side of the inspection platform, opposite the first side of the inspection platform;

a detector positioning system coupled to the detector and configured to move the detector on an abscissa axis, an ordinate axis, and an applicate axis;

an emitter positioning system operably coupled to the emitter and configured to move the emitter in the abscissa axis, the ordinate axis, and the applicate axis; and a controller coupled to the emitter positioning system and the detector positioning system, the controller being configured to receive at least one input from an interface, command the detector positioning system to move the detector to a reference point aligned with the emitter, the reference point being separated by a radius (ρ) on the applicate axis from an inspection point on the component indicated by the at least one input, and command the detector positioning system to move the detector to a detector position within a spherical dome centered on the reference point based on the at least one input, wherein the inspection platform and component are stationary.

2. The system of claim 1, wherein the detector positioning system is further configured to translate the detector in the abscissa axis, the ordinate axis, and the applicate axis, and rotate the detector about the abscissa axis and the ordinate axis such that the detector has five degrees of freedom.

3. The system of claim 1, wherein the controller is further configured to command the emitter positioning system to move the emitter in coordination with the detector to a point on the abscissa axis and the ordinate axis based on the inspection point.

4. The system of claim 1, wherein the detector positioning system is configured to rotate the detector about the abscissa axis and the ordinate axis such that a detector plane of the detector remains orthogonal to the inspection point.

5. The system of claim 1, wherein the controller is further configured to receive a first input of the at least one input, from the interface indicating the inspection point, the inspection point defining a position of the reference point on the abscissa axis and the ordinate axis;

receive a second input of the at least one input from the interface indicating a skewed viewing angle of the inspection point; and determine the detector position based on the second input.

6. The system of claim 1, wherein the emitter positioning system is configured to translate the emitter on the abscissa axis, the ordinate axis, and the applicate axis based on the reference point and the inspection point.

7. The system of claim 1, wherein the spherical dome is described by an arc extending from the reference point at the radius (ρ) from the inspection point to an articulation angle rotated about the applicate axis.

8. The system of claim 1, wherein the spherical dome extends in an arc away from the reference point rotated about the applicate axis, the arc being half of an emitter beam width.

9. The system of claim 1, wherein a touchscreen display is coupled to the interface and configured to:

display an image of the component, the image being at least one of an optical image and an inspection image; and receive the at least one inputs as one or more touch-based inputs based on the image indicating a portion of the component to be inspected.

10. The system of claim 5, wherein the controller is further configured to:

command the emitter positioning system to move the emitter and command the detector positioning system to move the detector based on the first input and the second input; and transmit information about the detector position to a display via the interface.

11. The system of claim 8, wherein the arc comprises an angular path of 15 to 45 degrees.

12. The system of claim 9, wherein the controller is further configured to determine the detector position based on the touch-based input.

13. A method for X-ray inspection of a component, the method comprising:

displaying an image of the component on a touch screen display;

while the component remains stationary:

receiving first input at the touch screen display indicating an inspection point on the component;

calculating, at a controller, a reference point aligned with the inspection point, the reference point having a position at a radius (ρ) on an applicate axis away from the inspection point;

moving a detector to the reference point, the detector being disposed on a first side of the component;

moving an emitter on an abscissa axis and an ordinate axis based on the inspection point, the emitter being disposed on a second side of the component opposite the first side;

receiving second input at the touch screen display indicating a skewed viewing angle of the inspection point;

calculating, at the controller, a detector position based on the skewed viewing angle, the detector position being located on a curved plane, the curved plane being described by a spherical dome having the radius (ρ) from the inspection point and centered on the reference point; and moving the detector to the detector position.

14. The method of claim 13, wherein the moving the detector to the detector position comprises:

translating the detector on the abscissa axis, the ordinate axis, and the applicate axis to the detector position; and rotating the detector about the abscissa axis and the ordinate axis to maintain the skewed viewing angle of the inspection point such that a detector plane of the detector is orthogonal to the inspection point.

15. The method of claim 13, further comprising moving the emitter on the applicate axis based on a zoom level indicated by one of the first input and the second input.

16. The method of claim 13, wherein the spherical dome is described by an arc extending from the reference point at the radius (ρ) from the inspection point to an articulation angle, the arc being rotated about the applicate axis.

17. The method claim 16, wherein the arc comprises a path along the spherical dome extending half of an emitter beam width.

18. A device for inspecting a component, the device comprising of:

an inspection platform configured to support the component;

an emitter disposed on a first side of the inspection platform, the emitter configured to emit an inspection beam toward the component;

a detector disposed on a second side of the inspection platform, opposite the first side, and configured to detect at least a portion of the inspection beam that penetrates the component;

a detector positioning system operably coupled to the detector and configured to move the detector on an abscissa axis, an ordinate axis, and an applicate axis;

an emitter positioning system operably coupled to the emitter and configured to move the emitter in the abscissa axis, the ordinate axis, and the applicate axis; and a controller operably coupled to the emitter positioning system and the detector positioning system, the controller configured to receive a first input indicating an inspection point on the component, command, via the detector positioning system, the detector to a reference point aligned with the inspection point, the reference point being separated by a radius (ρ) on the applicate axis from the inspection point, move the emitter to a point on the abscissa axis and the ordinate axis based on the inspection point, receive a second input indicating a modified viewing angle of the inspection point; and command, via the detector positioning system, the detector to a detector position within a spherical dome centered on the reference point, the spherical dome being defined by an emitter beam width and the radius (ρ), wherein the inspection platform and component are stationary.

19. The device of claim 18, wherein the controller is configured to receive the first input and the second input from a display coupled to the controller.

20. The device of claim 18, wherein the detector positioning system is further configured to provide five degrees of freedom to the detector in response to commands from the controller and maintain a detector plane of the detector in a position orthogonal to the inspection point.

21. The device of claim 18, wherein the detector position is located less than the radius (ρ) from the inspection point and away from the applicate axis, wherein commanding the detector to the detector position comprises moving the detector, using the detector positioning system, along the abscissa axis, the ordinate axis, and the applicate axis.

* * * * *